United States Patent
Shu et al.

(10) Patent No.: US 7,331,714 B2
(45) Date of Patent: Feb. 19, 2008

(54) OPTOMECHANICAL STRUCTURE FOR A MULTIFUNCTIONAL HARD X-RAY NANOPROBE INSTRUMENT

(75) Inventors: Deming Shu, Darien, IL (US); Jorg M. Maser, Oak Park, IL (US); Barry Lai, Woodridge, IL (US); Franz Stefan Vogt, Plainfield, IL (US); Martin V. Holt, Chicago, IL (US); Curt A. Preissner, Rosemont, IL (US); Robert P. Winarski, Lockport, IL (US); Gregory B. Stephenson, Lisle, IL (US)

(73) Assignee: UChicago Argonne, LLC, Chicago, IL (US)

( * ) Notice: Subject to any disclaimer, the term of this patent is extended or adjusted under 35 U.S.C. 154(b) by 103 days.

(21) Appl. No.: 11/238,196

(22) Filed: Sep. 29, 2005

(65) Prior Publication Data

US 2007/0071164 A1    Mar. 29, 2007

(51) Int. Cl.
*H05G 1/00* (2006.01)
*G21K 1/06* (2006.01)
*G01N 23/083* (2006.01)
*G01N 23/20* (2006.01)
*G01N 23/223* (2006.01)

(52) U.S. Cl. .................. 378/208; 378/44; 378/46; 378/51; 378/71; 378/79; 378/80; 378/84; 378/189

(58) Field of Classification Search .......... 378/43, 378/44, 45, 46, 51, 53, 57, 54, 62, 70, 74, 378/84, 87, 90, 71, 73, 79, 80, 189, 208
See application file for complete search history.

(56) References Cited

U.S. PATENT DOCUMENTS

| | | | | |
|---|---|---|---|---|
| 5,119,411 A | * | 6/1992 | Nakamura | 378/206 |
| 5,394,233 A | * | 2/1995 | Wang | 356/5.01 |
| 5,434,901 A | * | 7/1995 | Nagai et al. | 378/43 |
| 5,450,463 A | * | 9/1995 | Iketaki | 378/43 |
| 5,672,816 A | * | 9/1997 | Park et al. | 73/105 |
| 5,896,200 A | | 4/1999 | Shu | 356/373 |
| 6,167,112 A | * | 12/2000 | Schneider | 378/43 |
| 6,389,101 B1 | * | 5/2002 | Levine et al. | 378/85 |
| 6,504,896 B2 | * | 1/2003 | Miyake et al. | 378/34 |
| 6,607,840 B2 | | 8/2003 | Shu et al. | 428/591 |

(Continued)

OTHER PUBLICATIONS

Shu et al., "Design for an X-ray Nanoprobe Prototype with a Sub-10-nm Positioning Requirement," Synchrotron Radiation Instrumentation: Eight International Conference, edited by T. Warwick et al. vol. 705, May 12, 2004. pp. 1287-1290.*

(Continued)

*Primary Examiner*—Allen C. Ho
(74) *Attorney, Agent, or Firm*—Joan Pennington

(57) ABSTRACT

A multifunctional hard x-ray nanoprobe instrument for characterization of nanoscale materials and devices includes a scanning probe mode with a full field transmission mode. The scanning probe mode provides fluorescence spectroscopy and diffraction contrast imaging. The full field transmission mode allows two-dimensional (2-D) imaging and tomography. The nanoprobe instrument includes zone plate optics for focusing and imaging. The nanoprobe instrument includes a stage group for positioning the zone plate optics. The nanoprobe instrument includes a specimen stage group for positioning the specimen. An enhanced laser Doppler displacement meter (LDDM) system provides two-dimensional differential displacement measurement in a range of nanometer resolution between the zone-plate optics and the sample holder. A digital signal processor (DSP) implements a real-time closed-loop feedback technique for providing differential vibration control between the zone-plate optics and the sample holder.

16 Claims, 9 Drawing Sheets

U.S. PATENT DOCUMENTS

| | | | |
|---|---|---|---|
| 6,748,048 B2 * | 6/2004 | Dosho | 378/79 |
| 6,798,863 B2 * | 9/2004 | Sato | 378/46 |
| 6,822,733 B1 | 11/2004 | Shu | 356/152.3 |
| 6,920,696 B2 * | 7/2005 | Sawada et al. | 33/1 M |
| 2004/0187515 A1 | 9/2004 | Shu et al. | 62/378 |

OTHER PUBLICATIONS

Xiao et al., "Development of x-ray nanodiffraction instrumentation for studies of individual nano-objects," Nanotechnology 16 (2005), 1754-1760.*

Suzuki et al., "Diffraction-limited Microbeam with Fresnel Zone Plate Optisc in Hard X-Ray Regions," Jpn. J. Appl. Phys. vol. 40 (2001), 1508-1510.*

Yun et al., "Nanometer focusing of hard x rays by phase zone plates," Review of Scientific Instruments 70 (1999) 2238-2241.*

High-Precision Positioning Design for Synchrotron Radiation Instrumentation by Deming Shu, Conference Paper/ Keynote Presentation, May 20, 2004.

* cited by examiner

OPTOMECHANICAL STRUCTURE FOR A MULTIFUNCTIONAL HARD X-RAY NANOPROBE INSTRUMENT

CONTRACTUAL ORIGIN OF THE INVENTION

The United States Government has rights in this invention pursuant to Contract No. W-31-109-ENG-38 between the United States Government and Argonne National Laboratory.

FIELD OF THE INVENTION

The present invention relates to a multifunctional hard x-ray nanoprobe instrument. More specifically, the invention relates to a multifunctional hard x-ray nanoprobe instrument for installation on the Advanced Photon Source (APS) beamline to be provided as one of the characterization facilities for the Center for Nanoscale Materials (CNM) under construction at Argonne National Laboratory (ANL).

DESCRIPTION OF THE RELATED ART

A need exists for an effective hard x-ray probe for characterization of nanoscale materials and devices. A need exists for such a hard x-ray probe arranged to operate with photon energies, for example between 3 keV and 30 keV, with effective nanometer spatial resolution. Effective active vibration control in nanometer scale is significant for instruments, which need positioning resolution and stability in nanometer scale with a comparatively large travel range.

A need exists for a nanoprobe instrument which combines a scanning probe mode used for analytic studies of a small specimen area with a full-field transmission mode used for 2D and 3D imaging of the specimen at high resolution.

A principal aspect of the present invention is to provide an enhanced multifunctional hard x-ray nanoprobe instrument.

Other important aspects of the present invention are to provide such enhanced multifunctional hard x-ray nanoprobe instrument substantially without negative effect and that overcome some of the disadvantages of prior art arrangements.

SUMMARY OF THE INVENTION

In brief, a multifunctional hard x-ray nanoprobe instrument for characterization of nanoscale materials and devices is provided. The instrument includes a scanning probe mode with a full field transmission mode. The scanning probe mode provides fluorescence spectroscopy and diffraction contrast imaging. The full field transmission mode allows two-dimensional imaging and tomography. The nanoprobe instrument includes zone plate optics for focusing and imaging. The nanoprobe instrument includes a stage group for positioning the zone plate optics. The nanoprobe instrument includes a specimen stage group for positioning the specimen.

In accordance with features of the invention, the nanoprobe instrument includes a vacuum system with in-vacuum positioning of optics and the specimen. High-resolution positioning and scanning is performed using the stage group for zone plate optics. The specimen stage group is used for coarse positioning only.

In accordance with features of the invention, the nanoprobe instrument operates with photon energies between 3 keV and 30 keV. The focal length of the nanofocusing optics is provided in the range of 10-30 mm.

In accordance with features of the invention, the nanoprobe instrument includes an enhanced laser Doppler displacement meter (LDDM) system that provides two-dimensional differential displacement measurement in a range of nanometer resolution between the zone-plate optics and the sample holder.

In accordance with features of the invention, the nanoprobe instrument includes a base structure, which ensures stability on the nanometer scale with laser Doppler displacement meter (LDDM) closed-loop control. A plurality of laser heads and a plurality of reflection optics for the LDDM are mounted on the base structure to perform a two-dimensional differential measurement between the x-ray zone plate optics holder and the sample holder. The stage group for zone plate optics provide a three-dimensional positioning capability, for example, with 0.125 nm measuring resolution in 10 mm×10 mm×10 mm range. The stage group for zone plate optics includes a plurality of DC-motor driven translation stages and a PZT-driven high-stiffness horizontal stage and a PZT-driven high-stiffness vertical stage, each using overconstrained weak-link parallelogram mechanisms for ultraprecision motion control.

In accordance with features of the invention, the nanoprobe instrument includes a plurality of capacitance sensors arranged to dynamically measure the rotation axis angular and displacement shifts. The sample position is determined by the combination of the LDDM system and the capacitance sensors.

In accordance with features of the invention, the nanoprobe instrument includes a digital-signal-processor (DSP)-based real-time closed-loop feedback technique for providing differential vibration control between the zone-plate optics and the sample holder. A digital signal processor (DSP) computes the position differences between the two stage groups and determines the discrepancy between the actual and desired differential position, and performs a feed back for active vibration control.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

Figure 1:
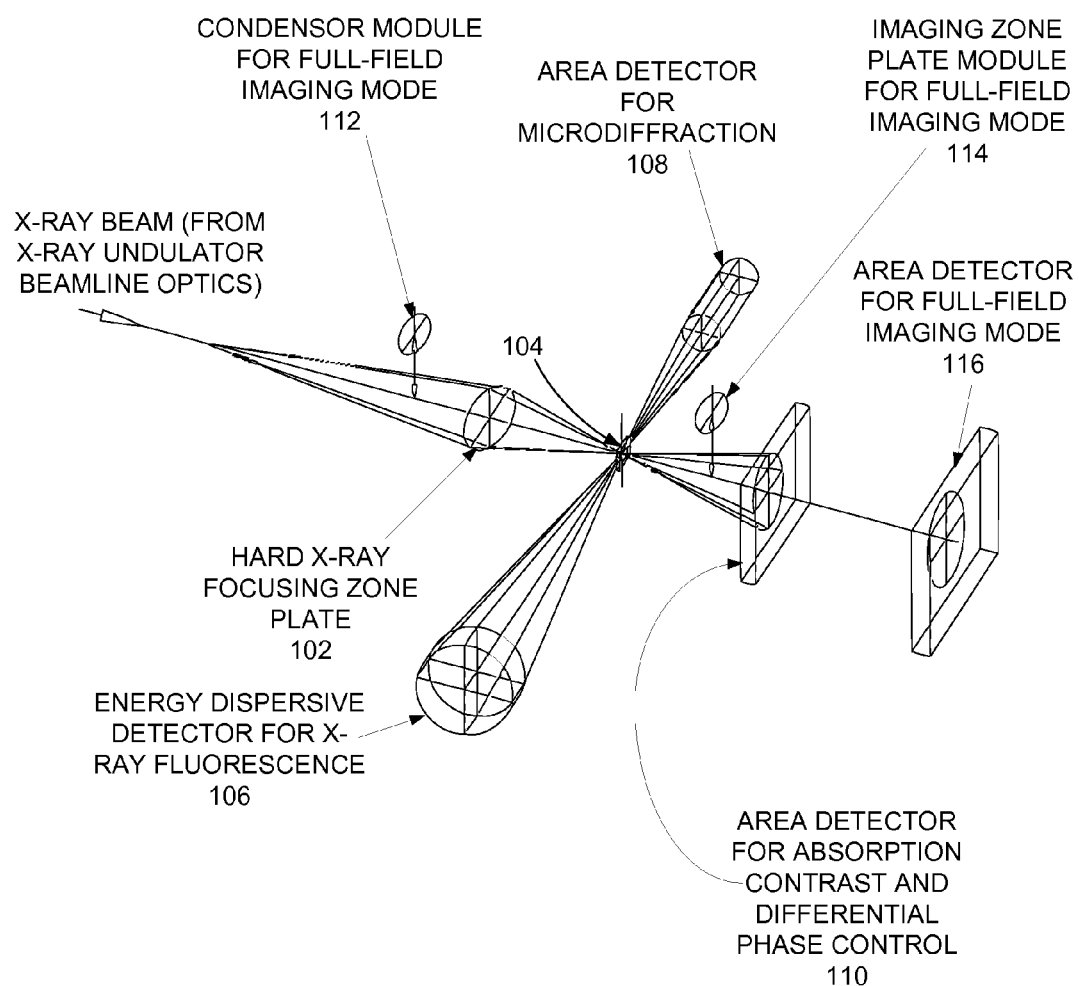
FIG. 1 is a schematic diagram representation of a multifunctional hard x-ray nanoprobe instrument in accordance with the preferred embodiment.

Having reference now to the drawings, in FIG. 1, there is shown a schematic diagram representation of a multifunctional hard x-ray nanoprobe instrument generally designated by the reference character 100 in accordance with the preferred embodiment. A hard x-ray nanoprobe beamline is being developed at the Advanced Photon Source (APS) and the beamline will house a multifunctional hard x-ray nanoprobe instrument 100, which is a new hard x-ray nanoprobe instrument that is one of the centerpieces of the characterization facilities of the Center for Nanoscale Materials (CNM) being constructed at Argonne National Laboratory (ANL).

In accordance with features of the preferred embodiment, the nanoprobe instrument 100 will operate with photon energies between 3 keV and 30 keV. The focal length of the nanofocusing optics will typically be in the range of 10-30 mm. The instrument 100 combines a scanning probe mode with a full-field transmission mode. The scanning probe mode provides fluorescence spectroscopy and diffraction contrast imaging. The full-field transmission mode allows two-dimensional (2-D) imaging and tomography.

Multifunctional hard x-ray nanoprobe instrument 100 receives an x-ray beam applied via a hard x-ray focusing zone plate 102 to a specimen 104. Nanoprobe instrument 100 combines a scanning probe mode with a full-field transmission mode. Nanoprobe instrument 100 includes an energy dispersive detector 106 using x-ray fluorescence for trace element mapping and spectroscopy, an area detector 108 for microdiffraction or x-ray diffraction to obtain local structural information such as crystallographic phase, strain texture, and an area detector 110 for absorption contrast and differential phase control or x-ray transmission in phase and absorption to image internal structures of complex devices. Nanoprobe instrument 100 includes a condensor module 12 for full-field imaging mode, an imaging zone plate module for full-field imaging mode 114, and an area detector 116 for full-field imaging mode.

In accordance with features of the preferred embodiment, major capabilities of the nanoprobe instrument 100 include: 1) scanning x-ray fluorescence spectroscopy, 2) transmitting x-ray microscope, and 3) x-ray micro-diffraction applications. A unique capability of the design of the nanoprobe instrument 100 is that once the sample 104 is in place, it is possible to do a complete characterization of the sample without further disturbing the sample.

In accordance with features of the preferred embodiment, major design enhancements that have been included into nanoprobe instrument 100 are: Diffractive optics, such as zone plates 102, will be used for focusing and imaging. The nanoprobe instrument 100 is designed as a vacuum system with in-vacuum positioning of optics and specimen. High-resolution positioning and scanning is performed using the stage group for zone plate optics. The specimen stage group is used for coarse positioning only. Position encoding is performed using a LDDM, with individual LDDMs measuring the position of each component with respect to a reference frame. A digital signal processor (DSP) computes the position differences between the two stage groups and determines the discrepancy between the actual and desired differential position, and performs a feed back for active vibration control. The scanning probe mode has a higher priority if the structure design needs a performance compromise between the scanning probe mode with full-field transmission mode.

In accordance with features of the preferred embodiment, the hard x-ray nanoprobe instrument 100 is one of the major characterization tools of Argonne Center for Nanoscale Materials. As such, nanoprobe instrument 100 will provide characterization of nanoscale materials and devices at the highest spatial resolution that can be achieved using hard x-ray optics. The system takes advantage of the good penetration of x-rays to study buried layers and interfaces. Nanoprobe instrument 100 uses x-ray fluorescence for trace element mapping and spectroscopy, x-ray diffraction to obtain local structural information such as crystallographic phase, strain texture, and x-ray transmission in phase and absorption to image internal structures of complex devices.

In accordance with features of the preferred embodiment, the potential uses of this invention will be x-ray microscopes using synchrotron radiation sources or other x-ray sources. This optomechical structure design may also be used for other microscopes or scientific instruments, such as electron microscopes and atomic force microscopes. The major advantage over existing products is that the optomechanical structure provides good active vibration control in nanometer scale. It is significant for instruments, which need positioning resolution and stability in nanometer scale with large travel range. This structure design also creates the feasibility for a nanoprobe instrument which combines a scanning probe mode used for analytic studies of a small specimen area with a full-field transmission mode used for 2D and 3D imaging of the specimen at high resolution.

Figure 2:
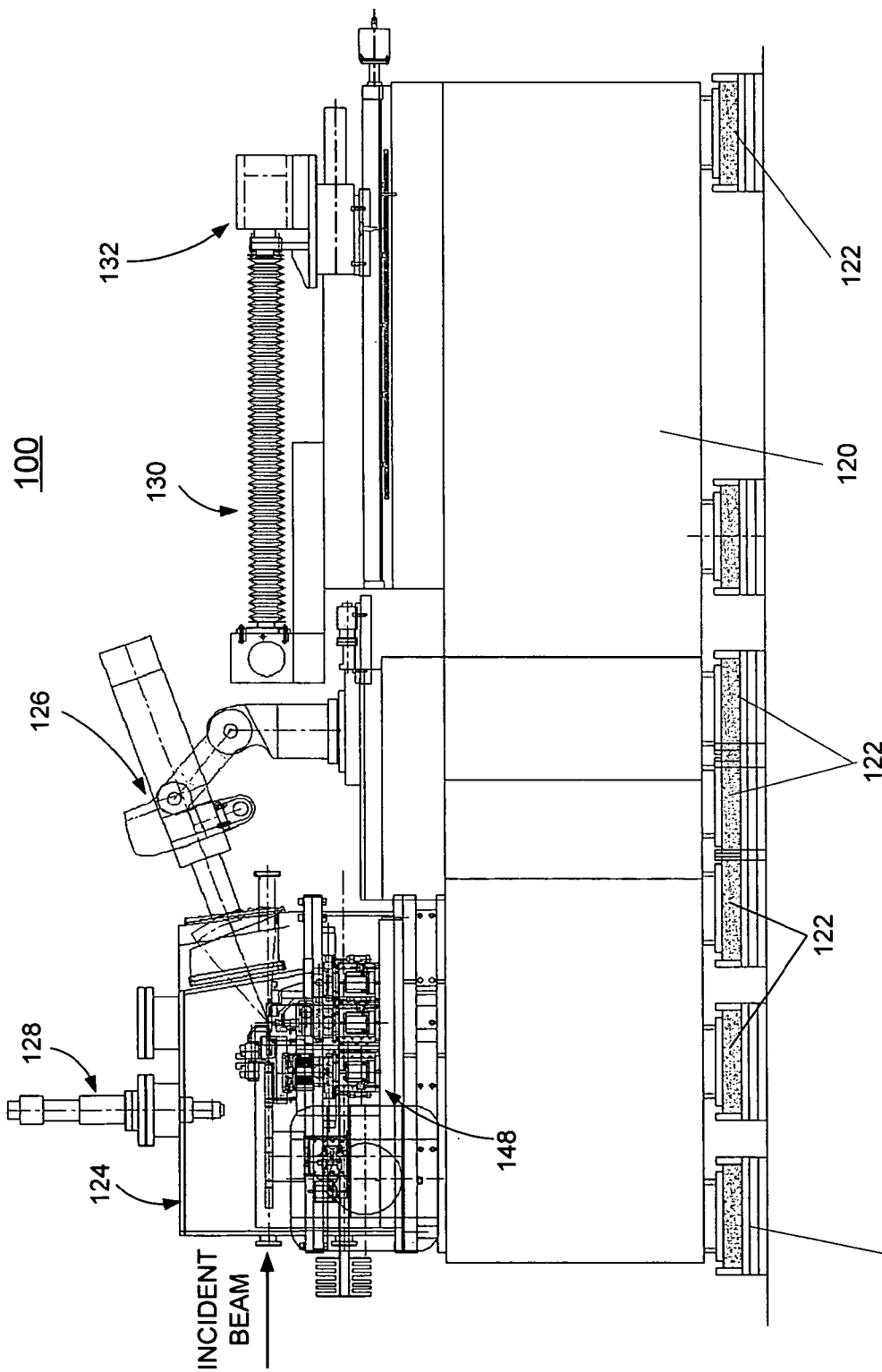
FIG. 2 is a side view illustrating an exemplary multifunctional hard x-ray nanoprobe instrument of FIG. 1 in accordance with the preferred embodiment.
Figure 3:
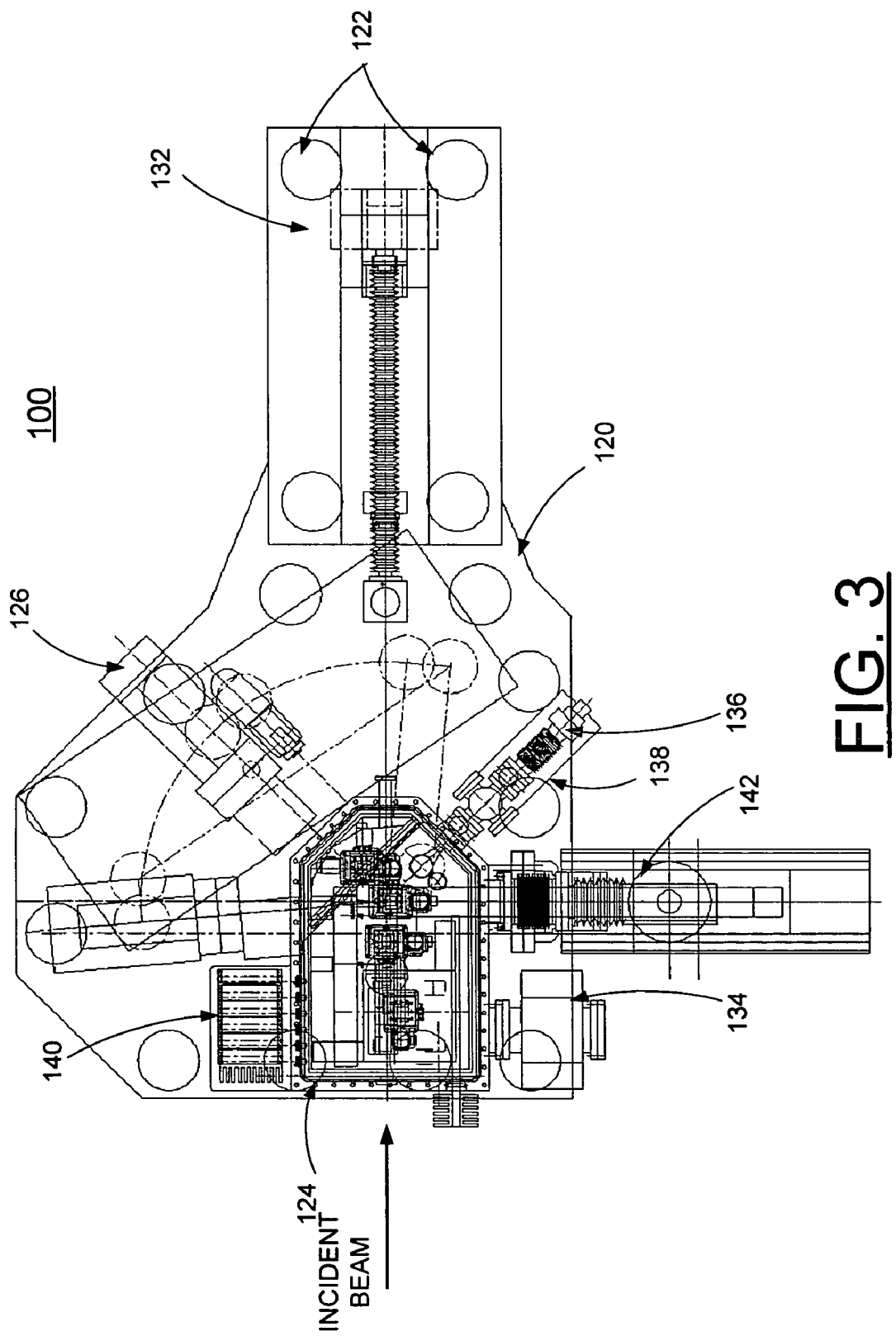
FIG. 3 is a top view illustrating an exemplary multifunctional hard x-ray nanoprobe instrument of FIG. 1 in accordance with the preferred embodiment.

Referring to FIG. 2 and FIG. 3, the optomechanical structure for the nanoprobe instrument 100 includes the following major component groups: a granite base 120 with a plurality of vibration isolators 122, an instrument vacuum chamber or vacuum vessel 124, a robotic detector manipulator 126 for microdiffraction, an upstream optical microscope 128, and a translation stage system 130 for a transmission imaging detector 132.

As can be seen in FIG. 3, at least one vacuum pump 134 is connected to the instrument vacuum chamber 124. An air lock 136 for specimen exchange is provided with a specimen or sample feedthrough 138. A laser head 140 for a laser Doppler displacement meter (LDDM) closed-loop control is located adjacent the instrument vacuum chamber 124. A detector for x-ray fluorescence microscope 142 is coupled to the instrument vacuum chamber 124.

Figure 4:
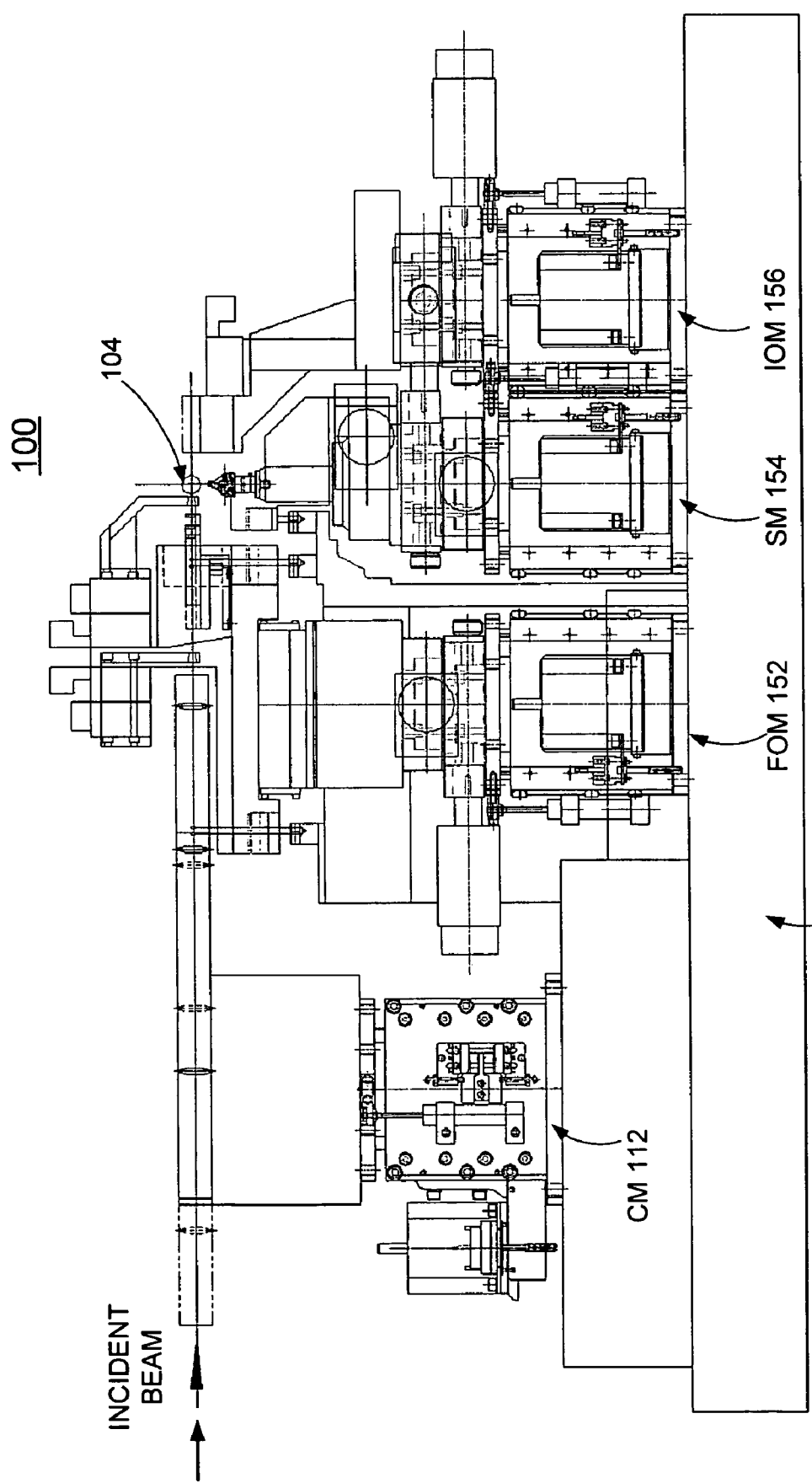
FIG. 4 is a side view illustrating exemplary positioning stage modules of the multifunctional hard x-ray nanoprobe instrument of FIG. 1 in accordance with the preferred embodiment.

Referring also to FIG. 4, inside the instrument vacuum chamber 124, a plurality of positioning stages for the optics are grouped into several subcomponents that are engineered to be moved in or out of the beam to allow configuration of the nanoprobe instrument 100 for scanning probe mode and full-field transmission mode. These subcomponents supported on a rigid support frame 148, such as a rigid Invar reference frame 148, include the condensor module (CM) 112, a focusing optics module (FOM) 152, a specimen module (SM) 154, and an imaging optics module (IOM) 156. The CM 112 provides illumination of the specimen 104 in full-field transmission mode. The FOM 152 provides positioning and scanning of the focusing zone plates 102 and order sorting aperture at high mechanical resolution and accuracy. The SM 154 provides specimen positioning and temperature control. The IOM 156 provides positioning of the objective zone plates and phase plates required for operation in full-field transmission mode. The FOM and SM form a scanning nanoprobe instrument. CM 112, SM 154, and IOM 156 form a transmission x-ray microscope (TXM). The SM 154 is shared by both configurations.

Figure 5:
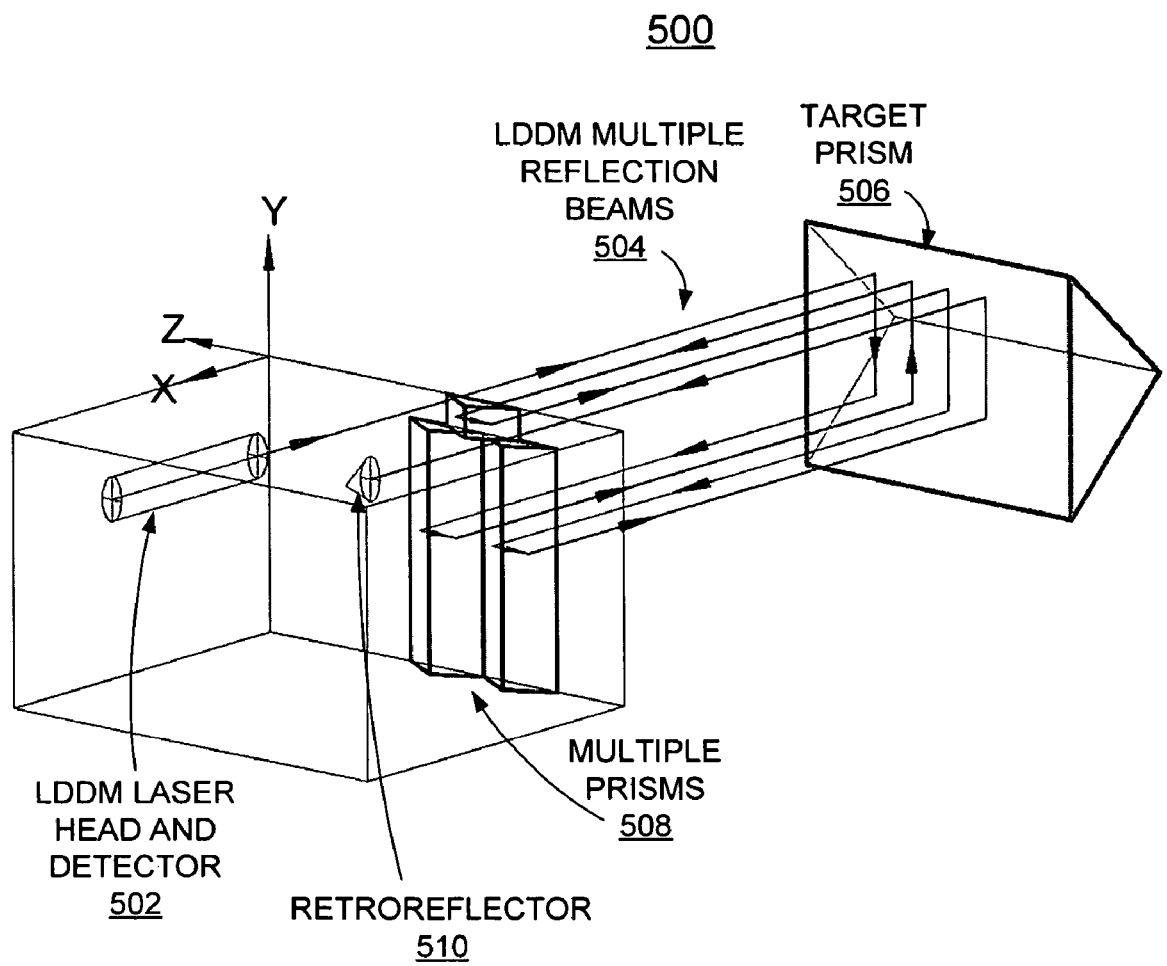
FIG. 5 is a schematic diagram representation of an exemplary self-aligning multiple-reflection optical design of the multifunctional hard x-ray nanoprobe instrument of FIG. 1 in accordance with the preferred embodiment.

Referring to FIG. 5, there is shown an exemplary self-aligning multiple-reflection optical design system generally designated by the reference character 500 of the multifunctional hard x-ray nanoprobe instrument 100 in accordance with the preferred embodiment. Self-aligning multiple-reflection optical design system 500 includes a LDDM laser source and detector electronics 502, a plurality of LDDM reflection beams 504, a target prism 506, a plurality of prisms 508, and a retroreflector 510. With the same LDDM laser source and detector electronics 502, the illustrated exemplary optical path provides eight times greater resolution.

The laser encoder system of the nanoprobe instrument 100 includes the rigid support Invar reference frame 148, a set of LDDMs, and laser optics for resolution extension, such as a pair of the illustrated self-aligning multiple-reflection optical design system 500 in FIG. 5. The LDDM is based on the principles of the Doppler effect and optical heterodyning. We have chosen a customized LDDM from Optodyne Inc. as our basic system, not only because of its high resolution, 2 nm, typically, and fast object speed, 2 m/s, but also because of its unique performance independent of polarization, which provides the convenience of creating a novel multiple-reflection-based optical design to attain subnanometer linear resolution. In the self-aligning multiple-reflection optical design for the LDDM system, the heterodyning detector is housed coaxially inside the frequency-stabilized laser source. Unlike a typical single reflection on the moving target, the laser beam is reflected back and forth eight times, or four times, between the fixed base and the moving target as shown in FIG. 5. The laser beam, which is reflected back to the heterodyning detector, is frequency-shifted by the movement of the moving target relative to the fixed base. With the same LDDM laser source and detector electronics, this optical path provides eight times (or four times) greater resolution for the linear displacement measurement and encoding. A 0.2 nm resolution has been reached by a prototype system. A total of eight LDDMs will be used to correct possible linear motion trajectory errors.

U.S. Pat. No. 6,822,733 issued to Deming Shu, Nov. 23, 2004 and assigned to the present assignee, discloses optical systems for laser encoder resolution extension with three-dimensional motion decoupling capability. The optical system includes a first prism mounted on a moving target, and a plurality of prisms, a retroreflector, a laser source, and a detector mounted on a fixed base. The moving target has three-dimensional linear motion freedom. The first prism on the moving target and the plurality of prisms and the retroreflector on the fixed base reflect a laser beam from the laser source to the detector define a three-dimensional optical path. The three-dimensional optical path provides multiple times optical resolution extension power for linear displacement measurement and encoding. This optic system is only sensible to the target motion on X direction and is substantially unaffected by movement in the Y and Z directions.

Figure 6:
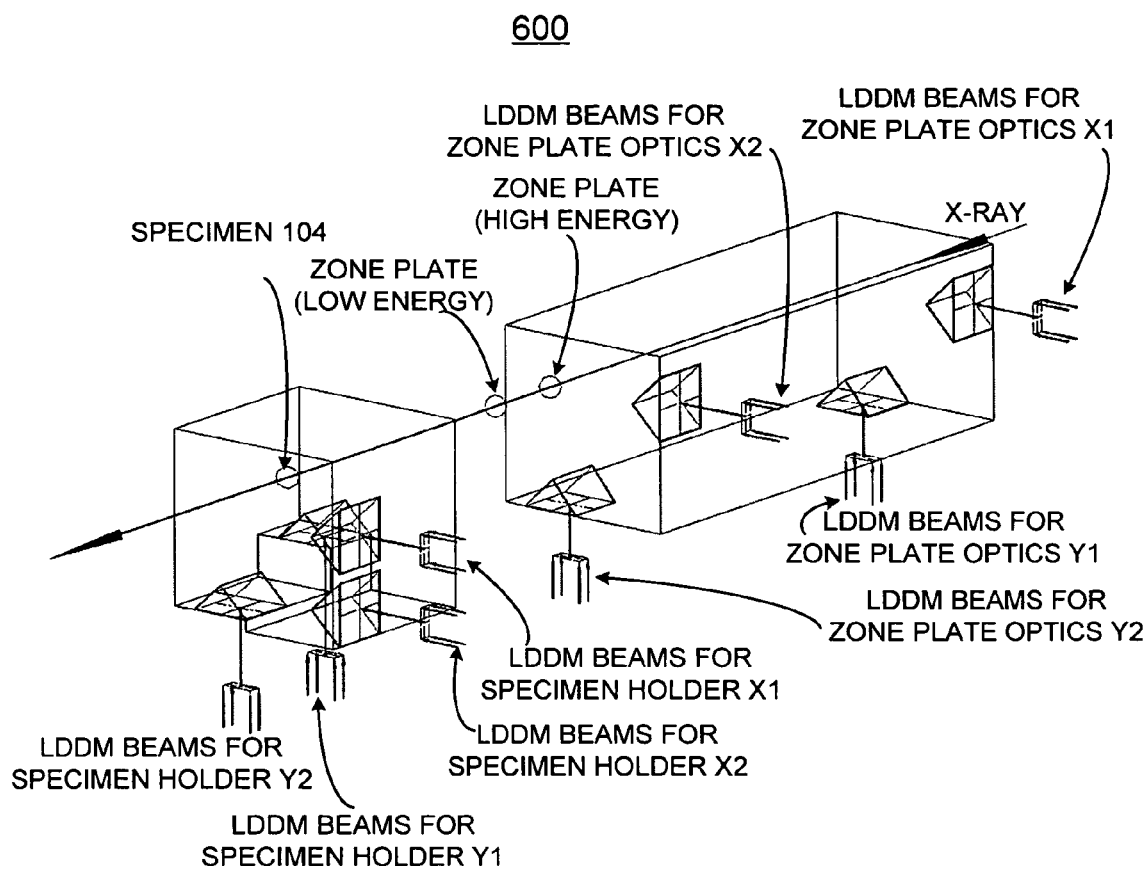
FIG. 6 is a schematic diagram representation of an exemplary eight laser Doppler displacement meter (LDDM) encoder system of the multifunctional hard x-ray nanoprobe instrument of FIG. 1 in accordance with the preferred embodiment.

Referring to FIG. 6, there is shown an exemplary eight laser Doppler displacement meter (LDDM) encoder system generally designated by the reference character 600 of the multifunctional hard x-ray nanoprobe instrument 100 in accordance with the preferred embodiment. LDDM encoder system 600 provides two-dimensional differential position encoding between the FOM 152 and the SM 154. The LDDM encoded travel ranges are, for example, 12 mm (X)×12 mm (Y)×12 mm (Z) for FOM and 12 mm (X)×12 mm (Y)×6 mm (Z) for SM.

Self-aligning multiple-reflection optical design system 600 advantageously is implemented in accordance with the disclosed optical systems of the above-identified U.S. Pat. No. 6,822,733. The subject matter of the above-identified U.S. Pat. No. 6,822,733 is incorporated herein by reference.

Figure 7:
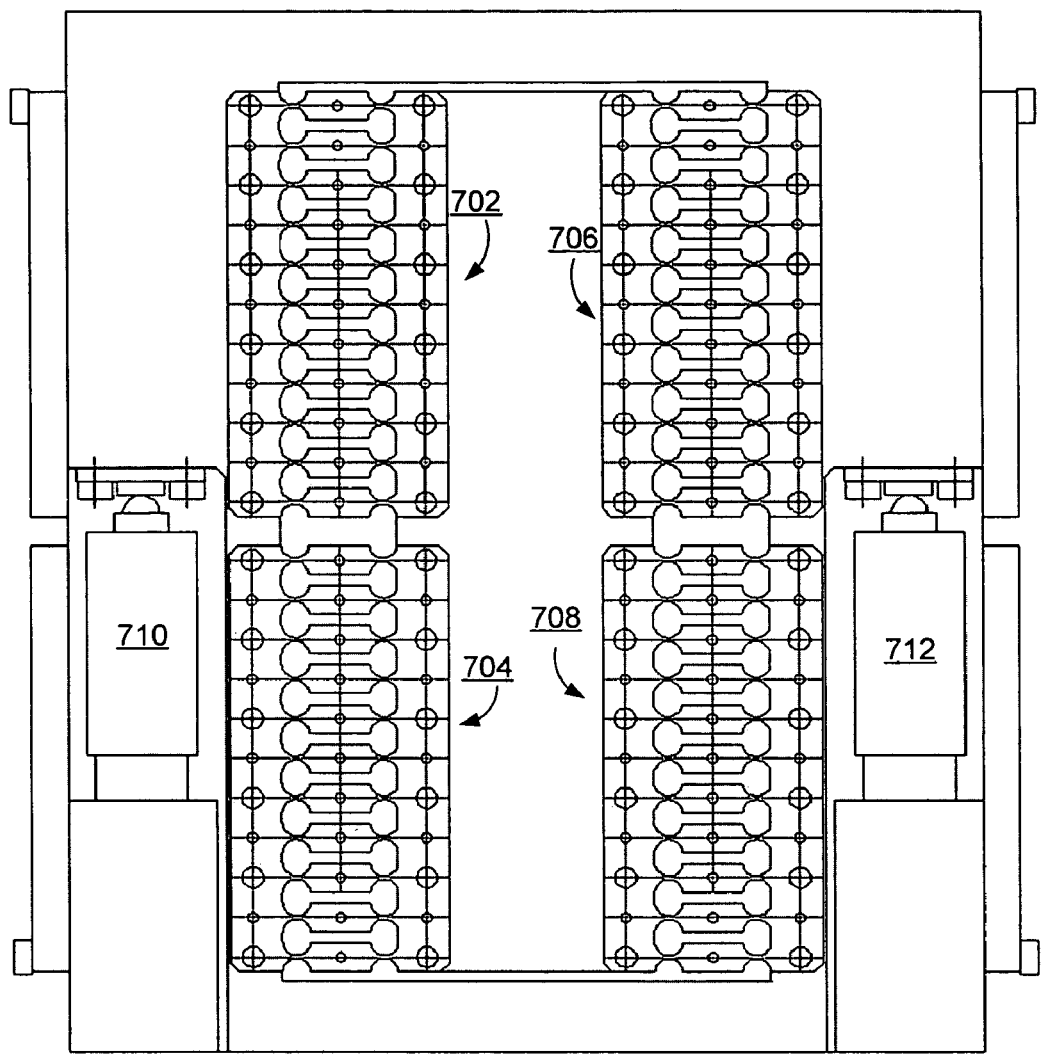
FIG. 7 is a plan view of an exemplary high stiffness horizontal PZT-stage of the multifunctional hard x-ray nanoprobe instrument of FIG. 1 in accordance with the preferred embodiment.

Referring to FIG. 7, there is shown an exemplary high stiffness horizontal PZT-stage generally designated by the reference character 700 of the multifunctional hard x-ray nanoprobe instrument 100 in accordance with the preferred embodiment. High stiffness horizontal PZT-stage 700 includes a plurality of weak-link groups 702, 704, 706, 708 and a pair of micro-actuators 710, 712.

Figure 8:
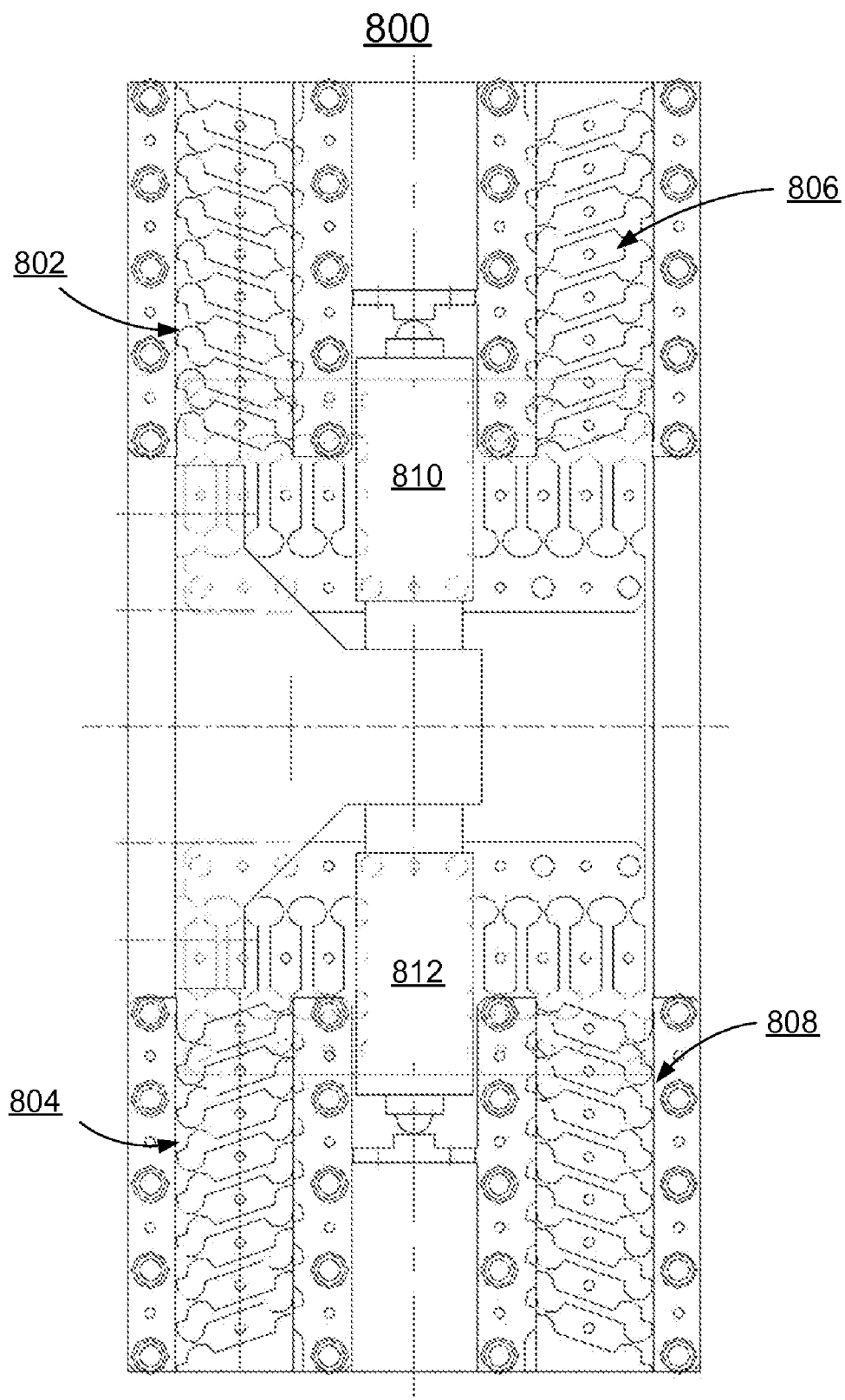
FIG. 8 is a plan view of an exemplary high stiffness vertical PZT-stage of the multifunctional hard x-ray nanoprobe instrument of FIG. 1 in accordance with the preferred embodiment.

Referring to FIG. 8, there is shown an exemplary high stiffness vertical PZT-stage generally designated by the reference character 800 of the multifunctional hard x-ray nanoprobe instrument 100 in accordance with the preferred embodiment. High stiffness horizontal PZT-stage 800 includes a plurality of weak-link groups 802, 804, 806, 808 and a pair of micro-actuators 810, 812.

U.S. Pat. No. 6,607,840 issued to Deming Shu, Thomas S. Toellner, and E. Ercan Alp, Aug. 19, 2003 and assigned to the present assignee, discloses redundantly constrained laminar structures as weak-link mechanisms and a novel method for manufacturing the redundantly constrained laminar structures as weak-link mechanisms. The method for producing the redundantly constrained laminar structures as weak-link mechanisms is carried out by lithographic techniques. A designed pattern is repeatedly chemically etched with a mask to produce a plurality of individual identical units. The units are stacked together to form the laminar structure and are secured together with fasteners. A high quality adhesive can be applied to the sides of the laminar structure to provide the mechanism equivalent to a single piece mechanism. The redundantly constrained laminar structures as weak-link mechanisms of the invention include a stack of a plurality of thin material structures. The stack of structures forming a laminar structure include multiple weak-link connections providing controllable movements in a plane of the layer and having a desired stiffness and stability. The plurality of thin material structures include predetermined locating-holes used with locating-pins to precisely stack the thin material structures together and are used with fasteners to secure the stack together.

Each of the high stiffness horizontal PZT-stage 700 and the high stiffness vertical PZT-stage 800 advantageously is implemented in accordance with the disclosed weak-link mechanisms of the above-identified U.S. Pat. No. 6,607,840. The subject matter of the above-identified U.S. Pat. No. 6,607,840 is incorporated herein by reference.

Figure 9:
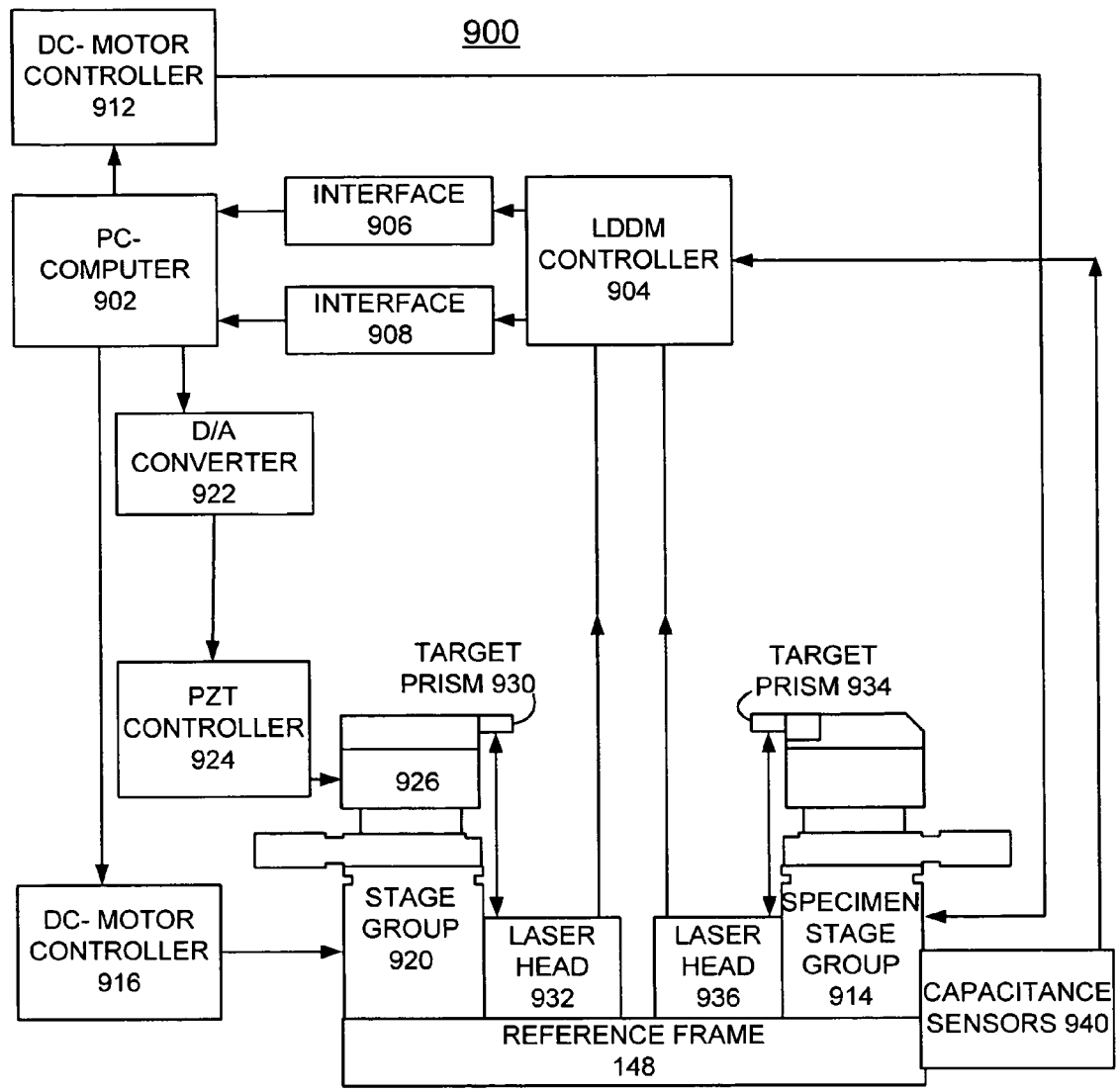
FIG. 9 is a schematic diagram representation of an exemplary feedback system for active vibration control in one direction of the multifunctional hard x-ray nanoprobe instrument of FIG. 1 in accordance with the preferred embodiment.

Referring to FIG. 9, there is shown an exemplary feedback system for active vibration control generally designated by the reference character 900 of the multifunctional hard x-ray nanoprobe instrument 100 in accordance with the preferred embodiment. Vibration control feedback system 900 provides active vibration control in one direction, such as the Y direction and a similar arrangement is implemented for active vibration control in the X direction. Vibration control feedback system 900 includes a two-dimensional differential laser Doppler displacement encoder system including a computer 902, such as a personal computer or digital signal processor (DSP) 902, coupled to a LDDM controller 904 via a pair of interface functions 906, 908. Personal computer or digital signal processor (DSP) 902 is coupled to a first DC-motor controller 912 that is coupled for operative control of a specimen stage group 914 for the specimen 104. Personal computer or DSP 902 is coupled to a second DC-motor controller 916 is coupled for operative control of providing a control signal to a stage group 920 for zone plate optics 102. Personal computer or DSP 902 is coupled to a digital-to-analog (D/A) converter 922. The D/A converter 922 is coupled a PZT controller 924 for a weak-link stage 926 of the stage group 920 for zone plate optics 102. LDDM controller 904 includes an optical path of a target prism 930 and a laser head 932 of the stage group 920 for zone plate optics 102. LDDM controller 904 includes an optical path of a target prism 934 and a laser head 936 of the specimen stage group 914 for the specimen 104.

The computer or digital signal processor (DSP) 902 computes the position differences between the two stage groups and determines the discrepancy between the actual and desired differential position, and performs a feed back for active vibration control. To improve the sample positioning accuracy for x-ray tomography applications, a plurality of capacitance sensors 940, for example, three pairs of capacitance sensors 940 were implemented to dynamically measure the rotation axis angular and displacement shifts. The sample position is determined by the combination of the LDDM system and the capacitance sensors 940.

A prototype instrument 100 has been developed with a LDDM controlled scanning stage system. An APS-designed, custom-built LDDM system provides two-dimensional differential displacement measurement between the zone-plate x-ray optics and the sample holder. One nm and 3 nm differential vertical and horizontal displacement steps, between the zone-plate holder and sample holder, have been demonstrated with closed-loop control.

A total of four sets of laser head and sixteen-reflection optics for the LDDM were mounted on the base structure to perform a two-dimensional differential measurement between the zone plate optics holder and the sample holder. The stages for zone plate optics provide a three-dimensional positioning capability with 0.125 nm measuring resolution in 10 mm×10 mm×10 mm range. The prototype instrument 100 includes three commercial DC-motor driven translation stages and two Argonne developed PZT-driven high-stiffness stages using over constrained weak-link parallelogram mechanisms for ultraprecision motion control as show in FIG. 7 and FIG. 8.

While the present invention has been described with reference to the details of the embodiments of the invention shown in the drawing, these details are not intended to limit the scope of the invention as claimed in the appended claims.

What is claimed is:

1. An optomechanical structure for a multifunctional hard x-ray nanoprobe instrument for characterization of a specimen including nanoscale materials and devices, said nanoprobe instrument including at least one first detector for a scanning probe mode for providing fluorescence spectroscopy and diffraction contrast imaging, and at least one second detector for a full field transmission mode for providing two-dimensional (2-D) imaging and tomography, said optomechanical structure for said nanoprobe instrument comprising:
   zone plate optics for focusing and imaging optical control;
   said zone plate optics including a hard x-ray focusing zone plate receiving a hard x-ray beam and applying focused x-rays to the specimen;
   said zone plate optics including subcomponents selectively moved in and out of the hard x-ray beam respectively for the scanning probe mode and the full field transmission mode;
   a stage group for positioning said subcomponents of said zone plate optics respectively for the scanning probe mode and the full field transmission mode; said stage group providing a three-dimensional positioning capability; said stage group including a plurality of DC-motor driven translation stages, a piezoelectric transducer (PZT)-driven high-stiffness horizontal stage and a PZT-driven high-stiffness vertical stage, each PZT-driven high-stiffness horizontal stage and vertical stage including overconstrained weak-link parallelogram mechanisms for precision motion control; and
   a specimen stage group for positioning the specimen; and said specimen stage group providing temperature control for the specimen.

2. The optomechanical structure for a multifunctional hard x-ray nanoprobe instrument as recited in claim 1 includes an instrument vacuum chamber containing the specimen, said zone plate optics, said stage group, and said specimen stage group.

3. The optomechanical structure for a multifunctional hard x-ray nanoprobe instrument as recited in claim 1 wherein said stage group for said zone plate optics enables high-resolution positioning and scanning with said three-dimensional positioning capability in a range of 10 mm×10 mm×10 mm and a measuring resolution of approximately 0.125 nm.

4. The optomechanical structure for a multifunctional hard x-ray nanoprobe instrument as recited in claim 1 wherein said specimen stage group is used for coarse positioning of a sample holder for the specimen relative to said zone plate optics.

5. The optomechanical structure for a multifunctional hard x-ray nanoprobe instrument as recited in claim 1 wherein the nanoprobe instrument operates with photon energies between 3 keV and 30 keV and wherein said zone plate optics has a focal length in the range of 10 mm and 30 mm.

6. The optomechanical structure for a multifunctional hard x-ray nanoprobe instrument as recited in claim 1 includes a laser Doppler displacement meter (LDDM) system for providing two-dimensional differential displacement measurement in a range of nanometer resolution between said zone plate optics and a sample holder for the specimen.

7. The optomechanical structure for a multifunctional hard x-ray nanoprobe instrument as recited in claim 6 includes a rigid support frame, said rigid support frame supporting said zone plate optics and said sample holder for providing stability on the nanometer scale for said zone plate optics and said sample holder for the specimen in combination with said laser Doppler displacement meter (LDDM) system.

8. The optomechanical structure for a multifunctional hard x-ray nanoprobe instrument as recited in claim 7 wherein said laser Doppler displacement meter (LDDM) system includes a plurality of laser heads and a plurality of reflection optics mounted on said rigid support frame.

9. The optomechanical structure for a multifunctional hard x-ray nanoprobe instrument as recited in claim 7 includes a capacitance sensor system including a plurality of capacitance sensors arranged to dynamically measure rotation axis angular and displacement shifts of the specimen.

10. The optomechanical structure for a multifunctional hard x-ray nanoprobe instrument as recited in claim 9 wherein a combination of the laser LDDM system and said capacitance sensor system determine sample position.

11. The optomechanical structure for a multifunctional hard x-ray nanoprobe instrument as recited in claim 7 includes a digital signal processor (DSP).

12. The optomechanical structure for a multifunctional hard x-ray nanoprobe instrument as recited in claim 11 wherein said digital signal processor (DSP) implements a real-time closed-loop feedback technique for providing differential vibration control between the zone-plate optics and the sample holder.

13. The optomechanical structure for a multifunctional hard x-ray nanoprobe instrument as recited in claim 1 includes a granite base supporting a vacuum vessel containing the specimen, said zone plate optics, said stage group, and said specimen stage group.

14. The optomechanical structure for a multifunctional hard x-ray nanoprobe instrument as recited in claim 13 includes a plurality of vibration isolators provided with said granite base.

15. The optomechanical structure for a multifunctional hard x-ray nanoprobe instrument as recited in claim 1 wherein said stage group for zone plate optics said piezoelectric transducer (PZT)-driven high-stiffness horizontal stage and said PZT-driven high-stiffness vertical stage includes a pair of micro-actuators provided with said overconstrained weak-link parallelogram mechanisms.

16. The optomechanical structure for a multifunctional hard x-ray nanoprobe instrument as recited in claim 7 wherein said rigid support frame supports a condensor module, said condenser module providing illumination of the specimen in the full field transmission mode.

\* \* \* \* \*